(12) United States Patent
Zyskowski

(10) Patent No.: US 7,652,158 B2
(45) Date of Patent: Jan. 26, 2010

(54) HIGH PURITY METAL ACETYLACETONATE COMPOUND

(75) Inventor: Chris Zyskowski, Ann Arbor, MI (US)

(73) Assignee: Nanoccrox, Inc., Ann Arbor, MI (US)

( * ) Notice: Subject to any disclaimer, the term of this patent is extended or adjusted under 35 U.S.C. 154(b) by 19 days.

(21) Appl. No.: 12/020,851

(22) Filed: Jan. 28, 2008

(65) Prior Publication Data

US 2008/0193350 A1 Aug. 14, 2008

Related U.S. Application Data

(60) Provisional application No. 60/886,781, filed on Jan. 26, 2007.

(51) Int. Cl.
*C07C 49/92* (2006.01)
*C07F 7/00* (2006.01)
*C07F 5/06* (2006.01)

(52) U.S. Cl. .............................. 556/40; 534/15; 556/54; 556/175

(58) Field of Classification Search ................ 423/21.1, 423/69, 111; 534/15; 556/54, 175, 40
See application file for complete search history.

(56) References Cited

U.S. PATENT DOCUMENTS

| | | | |
|---|---|---|---|
| 2,654,769 A | 10/1953 | Kozacik et al. | |
| 3,180,838 A | 4/1965 | Chiang | |
| 3,474,464 A | 10/1969 | Matthews et al. | |
| 4,617,408 A | 10/1986 | Nestler et al. | |
| 4,970,347 A | 11/1990 | Bellut | |
| 6,448,314 B1 | 9/2002 | Henrio | |
| 6,455,621 B1 | 9/2002 | Gay et al. | |

FOREIGN PATENT DOCUMENTS

CA 805698 2/1969

DE 1 475 826 1/1975

OTHER PUBLICATIONS

Mehrotra et al., Canadian Journal of Chemistry, vol. 39, pp. 795-798 (1961).*

* cited by examiner

*Primary Examiner*—Porfirio Nazario Gonzalez
(74) *Attorney, Agent, or Firm*—Gifford, Krass, Sprinkle, Anderson & Citkowski, P.C.; Avery N. Goldstein

(57) ABSTRACT

A process for producing a trivalent metal ion compound is provided. The process combines a trivalent metal organo-oxide $M\text{-}(OR^1)_3$ with a dione

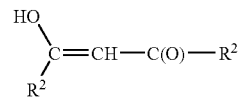

under reaction conditions to yield a reaction product (II)

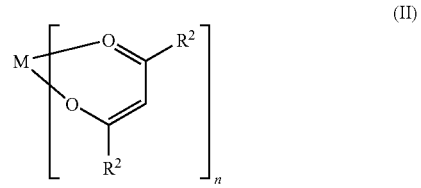

where $R^1$ in each occurrence independently is a $C_1$-$C_8$ alkyl, $C_6$-$C_{12}$ cycloalkyl, or $C_6$-$C_{14}$ aryl; $R^2$ in each occurrence independently is H, $C_1$-$C_8$ alkyl, $C_6$-$C_{12}$ cycloalkyl, or $C_6$-$C_{14}$ aryl; M is a trivalent main group or lanthanide metal ion of Al, Ga, In, Tl, Ce, Pr, Nd, Sm, Eu, Gd, Tb, Dy, Ho, Er, Tm, Yb, Zr, or Lu, and n is 3 with the proviso that when M is Zr n is 4. The reaction product has impurity levels of the order of tens of parts per million by weight when formed from reagent grade $M\text{-}(OR^1)_3$. The reaction product is isolated and freeze-dried without need for washing to preclude wash solution contamination.

14 Claims, No Drawings

HIGH PURITY METAL ACETYLACETONATE COMPOUND

CROSS REFERENCE TO RELATED APPLICATIONS

This application claims priority of U.S. Provisional Patent Application Ser. No. 60/886,781 filed Jan. 26, 2007, which is incorporated herein by reference.

FIELD OF THE INVENTION

The present invention relates in general to metal acetylacetonate compounds and in particular to a process for forming such compounds that results in a high degree of purity required for the production of high performance ceramo-optics.

BACKGROUND OF THE INVENTION

Trivalent metal ions are important components in a variety of materials requiring a high degree of purity. Representative of these materials are ceramo-optical materials such as terbium aluminum garnet, yttrium aluminum garnet and other trivalent rare earth aluminum garnets; gallium arsenide semiconductors, conductive nickel coatings such as indium oxides (ITO) and rare earth doped phosphors.

Many materials produced to date have not attained the desired properties predicted by theory owing to impurity levels within the material. These impurities manifest themselves as a decrease in material transparency, Verdet constant, K; semiconductor carrier density; semiconductor carrier mobility; and phosphor emission quench rates. These impurities are often traced to contaminants associated with trivalent metal compounds.

Thus, there exists a need for a process to produce a high purity trivalent metal compound that reduces impurity loading within the resultant compound. There also exists a need for a trivalent metal compound of high purity amenable to the fabrication of ceramo-optics, semiconductors and other materials that benefit from high precursor purity.

SUMMARY OF THE INVENTION

A process for producing an n-valent metal ion compound is provided. The process combines an n-valent metal organo-oxide $M\text{-}(OR^1)_n$ with a dione

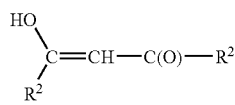

under reaction conditions to yield a reaction product

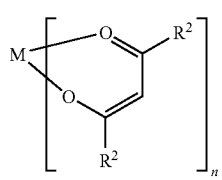

(II)

where $R^1$ in each occurrence independently is a $C_1$-$C_8$ alkyl, $C_6$-$C_{12}$ cycloalkyl, or $C_6$-$C_{14}$ aryl; $R^2$ in each occurrence independently is H, $C_1$-$C_8$ alkyl, $C_6$-$C_{12}$ cycloalkyl, or $C_6$-$C_{14}$ aryl; M is a trivalent main group or lanthanide metal ion of Al, Ga, In, Tl, Ce, Pr, Nd, Sm, Eu, Gd, Tb, Dy, Ho, Er, Tm, Yb, Zr, or Lu, and n is 3 with the proviso that when M is Zr n is 4. The reaction product has impurity levels of the order of tens of parts per million by weight when formed from reagent grade $M\text{-}(OR^1)_n$. The reaction product is isolated and freeze dried without need for washing to preclude wash solution contamination. The reaction product is especially advantageous as a metal oxide precursor for ceramo-optics and III-V semiconductors.

DETAILED DESCRIPTION OF THE INVENTION

The present invention has utility as a process for producing a high purity trivalent metal compound. The inventive compound is amenable to use to form a variety of materials that from part per million by weight (ppmw) impurities. These materials illustratively include optical grade aluminum garnets; spinets, semiconductor gallium arsenide, gallium aluminum arsenide, and aluminum oxide; trivalent lanthanide doped phosphors; and devices containing the same.

An inventive process is as follows:

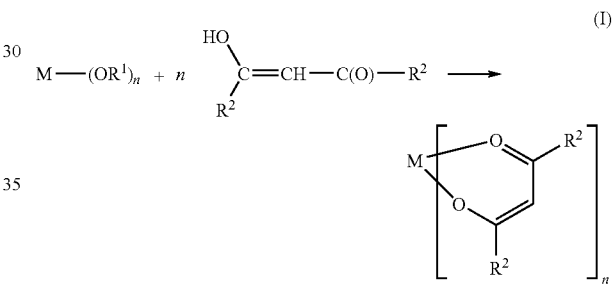

(I)

where $R^1$ in each occurrence independently is a $C_1$-$C_8$ alkyl, $C_6$-$C_{12}$ cycloalkyl, or $C_6$-$C_{14}$ aryl; $R^2$ in each occurrence independently is H, $C_1$-$C_8$ alkyl, $C_6$-$C_{12}$ cycloalkyl, or $C_6$-$C_{14}$ aryl; M is a main group or lanthanide metal ion of Al, Ga, In, Tl, Ce, Pr, Nd, Sm, Eu, Gd, Tb, Dy, Ho, Er, Tm, Yb, Zr or Lu; and n is 3 except when M is Zr, then n is 4. Preferably, $R^1$ is the $C_1$-$C_8$ alkyl and more preferably a $C_3$-$C_8$ branched alkyl. $R^2$ is preferably methyl.

It is appreciated that the hydrophilicity of the product according to reaction I decreases with increasing hydrophobicity of $R^2$. As a result, the hygroscopic propensity of the reaction I product is controlled.

The inventive reaction purifies trivalent metal ion reagents in preference to alkali metals, alkali earths, main group IV, V, VI and VII elements, as well as transition metals that are not trivalent; namely divalent, quadravalent, pentavalent and hexavalent ions. Without intending to be bound by a particular theory, differential solubility between trivalent metal ions and the aforementioned candidates as dione chelates is believed to be the basis for the purification relative to metal alkoxides. As a result, a reagent grade metal alkoxide having impurity levels of per Table 1 that produces a trivalent metal ion dione reaction product of structure (II) that has alkali metals, alkali earths, main group IV, V, VI and VII elements each present at less than 40 parts per million by weight (ppmw) and specific impurities of sulfur, lead, tin and trivalent zirconium at levels of less than 30, 10, 15 and 15 ppmw, respectively. The reaction product being

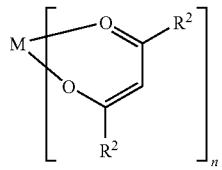
(II)

where $R^1$ in each occurrence independently is a $C_1$-$C_8$ alkyl, $C_6$-$C_{12}$ cycloalkyl, or $C_6$-$C_{14}$ aryl; $R^2$ in each occurrence independently is H, $C_1$-$C_8$ alkyl, $C_6$-$C_{12}$ cycloalkyl, or $C_6$-$C_{14}$ aryl; M is a trivalent main group or lanthanide metal ion of Al, Ga, In, Tl, Ce, Pr, Nd, Sm, Eu, Gd, Tb, Dy, Ho, Er, Tm, Yb, Zr, or Lu and n is 3 with the proviso that when M is Zr n is 4.

An additional benefit of the present invention is the ability to collect dry trivalent valent metal acetylacetonate without the need for washing, as wash solutions can impart impurities to the resultant compound that are leached from containers or other environmental sources.

Reaction I occurs in a solvent capable of dissolving the metal organo oxide M-$(OR^1)_n$ and the dione. Suitable solvents illustratively include alcohols such as methanol, ethanol, isopropanol, butanol, and pentanol; ethers such as $C_1$-$C_6$—O—$C_1$-$C_6$; alkanes such as hexanes, octanes, and petroleum distillates; and aromatics such as toluene, and xylenes. Preferably, the product of reaction I is insoluble in the solvent to facilitate isolation. $C_1$-$C_4$ alcohols represent a preferred set of solvents with the alcohol being neat.

The product of reaction I is amenable to dissolution in an appropriate solvent based on the hydrophilicity thereof and as such can be used in a solvated form to produce material that benefits from the improved purity of the compound by conventional techniques such as flame pyrolysis, or sol-gel formation. Alternatively, the product of reaction I is used as a material precursor in isolated form in processes such as chemical vapor deposition, and calcining. Isotactic compression of the resultant high purity metal oxide alone or as a mixture with other metal oxides, metals, or metal chelates achieves ceramo-optics of previously unattainable optical properties.

The present invention is further detailed with respect to the following non-limiting examples. While these examples illustrate purification with aluminum and gallium ions, it is appreciated that like results are obtained with other M trivalent ions.

EXAMPLE 1

6,615 g (66.1 mols) 2,4-pentanedione is combined at a level of 3.1 mol equivalents per mol of reagent grade Al(III) tri-sec-butoxide present in an amount of 5,250 g (21.3 mols). Ethanol is added in an amount equal to one-half the mass of Al(III) tri-sec-butoxide in a container immersed in an ice water bath at 0° C. The 2,4-pentanedione and ethanol are stirred to mix thoroughly. The Al(III) tri-sec-butoxide is slowly added while stirring, taking care not to let the mixture reach reflux. After approximately one-half of the Al(III)tri-sec-butoxide has been added to the solution, a white crystalline precipitate begins to form. Once the addition of the Al(III)tri-sec-butoxide is complete, the mixture is allowed to cool while stirring is continued. Upon warming to room temperature of 20° C., the product is isolated by filtration and then dried. Further washings are not required. The material is then dried in a freeze dryer to yield an off-white crystalline solid of Al(III) acetylacetonate. The yield of the above-described process is approximately 97% mol. This reaction is summarized in scheme III.

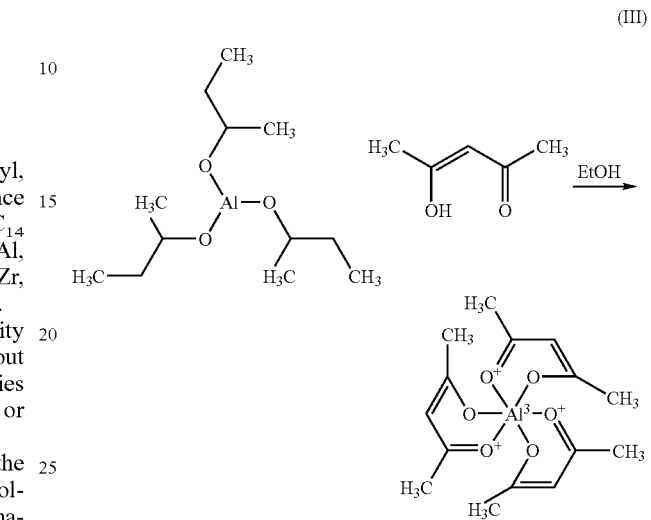
(III)

Table 1 below provides a spark source mass spectrograph (SSMS) chemical analysis of an Al(III) acetylacetonate produced per the present invention. As shown in this table, undesirable impurities such as sulfur, lead, tin and zirconium are held to levels below the detection level of the SSMS chemical analysis method as compared to the reagent grade precursor that fails to achieve the desired purity levels. In this manner, a high purity Al(III)acetylacetonate is produced.

TABLE 1

Inductively coupled plasma-mass spectrometry analysis of reagent grade Al(III)tri-sec-butoxide and Al (acac) (II) provided by reaction scheme III for selected trace elements.

| Analysis | Al(III)tri-sec butoxide/Al (acac) ppmw |
|---|---|
| Li | <0.5 |
| Be | Interference |
| B | 1.2/0.2 |
| F | <5 |
| Na | 2 |
| Mg | <10 |
| Al | Major |
| Si | 30 |
| P | ≦1 |
| S | ≦25 |
| Cl | 7 |
| K | 15 |
| Ca | 15 |
| Ti | ≦10 |
| V | 1.7/<1 |
| Cr | <10 |
| Mn | ≦1 |
| Fe | 10/5 |
| Co | <1 |
| Ni | <10 |
| Cu | ≦1 |
| Zn | <10 |
| Ga | 2.6/<2 |
| Zr | <10 |

TABLE 1-continued

Inductively coupled plasma-mass spectrometry analysis of reagent grade Al(III)tri-sec-butoxide and Al (acac) (II) provided by reaction scheme III for selected trace elements.

| Analysis | Al(III)tri-sec butoxide/Al (acac) ppmw |
|---|---|
| Mo | <10 |
| Sn | <10 |
| Sb | <5 |
| Ba | <5 |
| La | <1 |
| Ce | <5 |
| Pb | <5 |

EXAMPLE 2

The procedure of Example 1 is repeated with gallium tri-terbutoxide in metric substitution for the Al(III) tri-sec-butoxide thereof to yield a comparable quality of acetylacetonate as determined by SSMS.

EXAMPLE 3

The process of Example 1 is repeated with 2,4-octanedione in stoichiometric substitution for the 2,4-pentanedione thereof and the substitution of octanol for ethanol thereof to yield an analogous aluminum 4-ketobutylacetonate.

The foregoing description is illustrative of particular embodiments of the invention, but is not meant to be a limitation upon the practice thereof. The following claims, including all equivalents thereof, are intended to define the scope of the invention.

Although described with respect to one embodiment, changes in the processing parameters that would be known to those skilled in the art are also included in the present invention.

The invention claimed is:

1. A process for producing an n-valent metal ion compound comprising:

combining an n-valent metal organo-oxide $M\text{-}(OR^1)_n$ with a dione

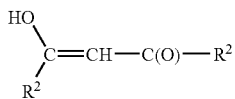

under reaction conditions in an alcohol solvent to yield a reaction product

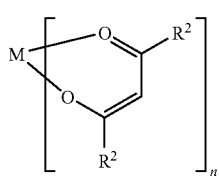

where $R^1$ in each occurrence independently is a $C_1$-$C_8$ alkyl, $C_6$-$C_{12}$ cycloalkyl, or $C_6$-$C_{14}$ aryl; $R^2$ in each occurrence independently is H, $C_1$-$C_8$ alkyl, $C_6$-$C_{12}$ cycloalkyl, or $C_6$-$C_{14}$ aryl; M is a trivalent main group or lanthanide metal ion of Al, Ga, In, Tl, Ce, Pr, Nd, Sm, Eu, Gd, Tb, Dy, Ho, Er, Tm, Yb, Zr, or Lu, and n is 3 with the proviso that when M is Zr n is 4; and collecting dry the reaction product II as a filtered precipitate from the alcohol solvent.

2. The process of claim 1 wherein M is Al.

3. The process of claim 1 wherein $R^1$ in each occurrence is a $C_1$-$C_8$ alkyl and $R^2$ in each occurrence is a $C_1$-$C_8$ alkyl.

4. The process of claim 1 wherein the reaction conditions are an atmosphere of air and in a solvent at a temperature at which the solvent is liquid.

5. The process of claim 4 wherein the temperature is below 20° Celsius.

6. The process of claim 1 wherein the reaction product II is collected as a filtered precipitate and used to form a ceramo-optic without washing.

7. The process of claim 1 wherein the reaction product II has impurity levels of sulfur less than 30 parts per million weight.

8. The process of claim 1 wherein the reaction product II has impurity levels of lead less than 10 parts per million weight.

9. The process of claim 1 wherein the reaction product II has impurity levels of tin less than 15 parts per million weight.

10. The process of claim 1 wherein the reaction product II has impurity levels of zirconium less than 15 parts per million weight.

11. The process of claim 7 wherein

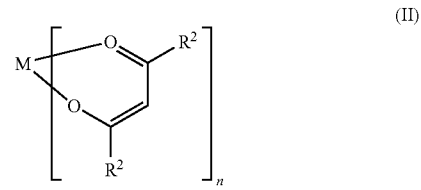

has less than 40 parts per million weight of alkali metals, alkali earths, main group IV, V, VI and VII elements, divalent transition metals and quadravalent transition metals.

12. A process for producing high purity Al(III)acetylacetonate comprising:

stirring together 2,4-pentanedione with ethanol in a container immersed in an ice water bath;

adding Al(III)tri-sec-butoxide to said 2,4-pentanedione and said ethanol being stirred in said container immersed in said ice water bath;

allowing sufficient time for said Al(III)tri-sec-butoxide to react with said 2,4-pentanedione to form a mixture;

filtering and drying said mixture to isolate a crude Al(III) acetylacetonate compound; and freeze drying said mixture to obtain a high purity Al(III) acetylacetonate compound having impurity levels alkali metals, alkali earths, main group IV, V, VI and VII elements each present at less than 40 parts per million by weight (ppmw) and specific impurities of sulfur, lead, tin and trivalent zirconium at levels of less than 30, 10, 15 and 15 ppmw.

13. The process of claim 12 wherein the crude Al(III) acetylacetonate compound is freeze dried without prior washing.

14. The process of claim 1 wherein the alcohol solvent is a $C_1$-$C_4$ alcohol.

* * * * *